United States Patent [19]

Binns et al.

[11] Patent Number: 5,332,676

[45] Date of Patent: Jul. 26, 1994

[54] AVIPOX VIRUS PROMOTER

[75] Inventors: Matthew M. Binns; Michael E. G. Boursnell, both of Huntingdon, England; Joan I. A. Campbell, Lagos, Nigeria

[73] Assignee: British Technology Group Limited, London, England

[21] Appl. No.: 820,656

[22] PCT Filed: Jul. 26, 1990

[86] PCT No.: PCT/GB90/01156

§ 371 Date: Jan. 17, 1992

§ 102(e) Date: Jan. 17, 1992

[87] PCT Pub. No.: WO91/02072

PCT Pub. Date: Feb. 21, 1991

[30] Foreign Application Priority Data

Jul. 26, 1989 [GB] United Kingdom ............ 8917059.1

[51] Int. Cl.$^5$ ............ C12N 15/11; C12N 15/86; C12N 15/39; C12N 7/01

[52] U.S. Cl. .................. 435/320.1; 536/24.1; 536/23.72; 435/235.1; 935/6

[58] Field of Search ............ 435/235.1, 320.1, 172.3, 435/240.2; 536/27, 23.72, 24.1; 424/89, 93; 935/6, 34, 36, 57, 65, 70

[56] References Cited

FOREIGN PATENT DOCUMENTS

WOA89/038-79  5/1989 PCT Int'l Appl. .......... C12N 15/00

OTHER PUBLICATIONS

Binns, M. M. et al. 1987 Nucleic Acids Res. vol. 15 pp. 6563–6573.
Binns, M. M. et al. 1989 *Virology* vol. 170 pp. 288–291.
Van Meir, E. et al. 1988, *Arch. Virol* vol. 102 pp. 19–27.
Boyle, D. B. et al. 1988, *Virus Research* vol. 10 pp. 343–356.

*Primary Examiner*—Richard A. Schwartz
*Assistant Examiner*—Mary E. Mosher
*Attorney, Agent, or Firm*—Nixon & Vanderhye

[57] ABSTRACT

Fowlpox virus (FPV) or other avipox virus promoter DNA for use in expressing a foreign gene inserted in a FPV vector by homologous recombination, which comprises the promoter of the following 4a gene, said 4a gene encoding a protein of very roughly about 890 amino acids in a sequence beginning Met Met Leu Ile Lys Asn Ile Val Thr Leu
Asp Gln Leu Glu Ser Ser Asp Tyr Leu Tyr.

8 Claims, No Drawings

1

AVIPOX VIRUS PROMOTER

BACKGROUND OF THE INVENTION

1. Field of the Invention

The invention is in the field of recombinant DNA technology and relates to avipox promoters useful for the expression of foreign DNA inserted into a fowlpox virus vector.

2. Description of the Prior Art

Poxviruses are large viruses with a complex morphology containing linear double-stranded DNA genomes. They are among the few groups of DNA viruses that replicate within the cytoplasm of the cell. They are subclassified into six genera: orthopoxviruses, avipoxviruses, capripoxviruses, leporipoxviruses, parapoxviruses and entomopoxviruses. Vaccinia virus (VV), an orthopoxvirus, is the most widely studied of the poxviruses, and is the subject of U.S. Pat. No. 4,603,112 (Paoletti et al.,). Fowlpox virus (FPV) is an avipoxvirus or arian poxvirus.

Recent advances in recombinant DNA technology have allowed VV to be used as a vector to carry and express foreign genes. Foreign DNA is introduced into the VV genome by a process of homologous recombination. Homologous recombination involves essentially (1) pre-selecting a length of the VV genome in some region which does not impair the replication and normal functioning of the virus (hereinafter called a "non-essential region"), (2) making a construct comprising a VV promoter and a length of foreign DNA within a copy of the non-essential region (NER) so that the foreign DNA is under the control of the promoter and so that the promoter-foreign DNA combination is flanked by extensive sequences of non-essential region of VV DNA, (3) co-infecting appropriate tissue culture cells with the VV and with the construct and (4) selecting cells containing VV in which the pre-selected length has been recombined in vivo so that it is replaced in the genome by the construct DNA. The recombinant VV expresses the foreign gene in vivo, stimulating the immunity to the protein in an appropriate host. The procedure has considerable potential for use in vaccination.

More recently, similar technology has been applied to fowlpox virus (FPV). Although VV promoters have been used successfully in laboratory constructs of FPV, it is undesirable to incorporate elements of such VV, an orthopoxvirus which has a wide host range recombinant vaccine, for fear of recombination events which could pose a health risk. There is therefore a need to develop FPV promoters for use in recombinant FPV. Certain FPV promoters have been described in UK Patent Application Publication No. 2211504A or PCT Application WO/89/03879 (NRDC). However, each promoter has its own peculiar characteristics of strength and timing of promotion. A choice of promoters is therefore very highly desirable.

One of the major proteins of VV is the 4a core protein, DNA coding for which has been sequenced by E. Van Meir and R. Wittek, Archives of Virology 102, 19–27 (1988). The mRNA for such a protein might be strongly promoted if it exists in FPV. The task of locating and cloning new FPV promoters is made more difficult because only very limited data have been published about the DNA sequence of the FPV genome. A greater amount of the VV genome has been sequenced, but the FPV genome is much larger than that of VV. Estimates have put it at from 240 to 360 kbp compared with 186 kbp in VV. There is no publicly available library of FPV DNA. Homologies and heterologies between a few parts of the FPV and VV genomes are known.

SUMMARY OF THE INVENTION

It has now been found that FPV does have a counterpart to the 4a protein of VV and that it is preceded by a strong promoter.

The science of promoters of poxvirus DNA is at present poorly understood. It is known that certain regions to the 5' or "upstream" end of a gene serve to assist in transcribing genomic DNA into messenger RNA by binding the RNA polymerase involved in the transcription so that the mRNA which contains the start codon of the gene can be transcribed. Such upstream regions are referred to as the "promoter". It is often not possible a priori to say for certain which nucleotides of the upstream sequence are essential and which are inessential for promotion, nor is the minimum or maximum length of the promoter known with great precision. Although this lack of precision in the whereabouts and length of the promoter might at first sight seem rather unsatisfactory, it is not a problem in practice, since there is normally no harm in Including additional DNA beyond the region which serves to transcribe the DNA. Further as described later, it is possible by tedious experiment to determine this region more precisely. In all these circumstances, it is therefore more appropriate to define the promoter by reference to the gene which it precedes, rather than by reference to the sequence of the promoter.

The 4a gene can be defined in various ways, always remembering, of course, that there will doubtless be minor differences in its sequence between one strain or type of FPV and another, or between different avipoxviruses. One convenient, arbitrary, way of defining it is by reference to an appropriate length of the amino acid sequence which it encodes. It may reasonably be assumed that the first 20 or, more preferably, the first 30 amino acids, say, would form a unique sequence in FPV. Accordingly, one convenient definition of the FPV 4a gene is the gene which encodes a protein of 800–1000 amino acids (especially 860–920 amino acids) in a sequence (SEQ ID NO: 1) beginning Met Met Leu Ile Lys Asn Ile Val Thr Leu Asp Gln Leu Glu Ser Ser Asp Tyr Leu Tyr.

It will be appreciated, of course, that variations in the first 20 amino acids are likely to occur between different FPV strains. Probably there would be at least 90% homology over the whole gene, but there may well be less homology over the first 20 amino acids, perhaps up to 3 or 4 differences. It is confidently believed, however, that no one skilled in the field will be in any doubt as to which gene is intended, whatever the precise degree of aberration in the amino acid sequence of the first 20 or 30.

The FP4a gene is believed to lie in a central region of the genome, but its location is unknown at present. Applicants have identified it by a laborious procedure which comprised making a random library of part of the FPV genome, sequencing it, comparing the sequences with those of the VV 4a gene, and fortunately finding that sequences having some degree of homology were present in the library. Although the degree of homology at the amino acid level measured over the first 302 amino acids, was only 33%, successful identification was achieved.

The invention includes a DNA molecule which consists substantially of the non-coding DNA to the 5'-end of the 4a gene and comprising the promoter thereof. "Non-coding" means not coding for the 4a gene: it could code for another gene (and appears to do so) as well as serving as a promoter for the 4a gene. Any reasonable length of such DNA, typically up to 200, usually up to 160, and especially up to 100 nucleotides (or base-pairs in the case of ds DNA) of the 5'-end (even if it codes for DNA within the next gene along the genome), is herein referred to as "promoter DNA".

The invention also includes a recombination vector comprising a cloning vector containing a non-essential region (NER) sequence of FPV, said NER being interrupted by DNA which consists of or includes (a) promoter DNA of the invention, followed by (b) a foreign gene (i.e. a gene which it is desired to insert into the FPV vector) transcribable by the promoter.

In one particular aspect, the invention includes a recombination vector which comprises in order:
(1) a first homologously recombinable sequence of the fowlpox virus (FPV) genome,
(2) a sequence within a first portion of a non-essential region (NER) of the FPV genome,
(3) promoter DNA according to the invention,
(4) a foreign gene transcribably downstream of the promoter (whereby when the fowlpox virus RNA polymerase binds to the promoter it will transcribe the foreign gene into mRNA) and
(5) a sequence within a second portion of the same NER of the FPV genome, the first and second sequences being in the same relative orientation as are the first and second portions of the NER within the FPV genome, and
(6) a second homologously recombinable sequence of the FPV genome, said sequences (1) and (6) flanking the NER in the FPV genome and being in the same relative orientation in the recombination vector as they are within the FPV genome.

In another aspect, the invention includes a DNA construct which comprises a promoter of the invention transcribably linked to a foreign gene. Such a construct or "cassette" can be inserted in a cloning vector, which can then be used as a recombinant vector useful in preparing a recombination vector of the invention.

The invention further includes hosts harbouring the recombination and recombinant vectors of the invention, especially a bacterial host harbouring a plasmid vector.

The invention is further directed to a recombinant FPV which is the product of homologous recombination of FPV with a recombination vector of the invention containing a foreign gene; the process of homologous recombination; animal cells infected with such a recombinant FPV; a process of in vitro culture of these infected cells; and a method of vaccinating a responsive animal, especially a chicken, which comprises inoculating it with the recombination vector of the invention.

DESCRIPTION OF THE PREFERRED EMBODIMENTS

While the precise length of DNA required for promotion is not known, it is generally reckoned to be up to 100 base pairs from the RNA start site, but this can be as much as 60 base pairs away from the gene start site (the ATG codon). Accordingly a DNA sequence contained within 160 base pairs, less preferably 100 bp, to the 5'-end of the gene (immediately preceding the start codon) is of particular interest for the purposes of the invention. The DNA sequences of these 160 base pairs are shown below (arbitarily divided into blocks of 10 for ease of reading) for the FPV 4a and in the 5' to 3' direction.

```
ACAACATTTA TAGTCTTGAG TGCTGATAAC TGTCCGTTAG TAAGTTCATA GTTTTTATTA
CACGGATATA CGTCTTCTGA AAAGGCTGTT AAGTTATATT CTTTGGCTAT ATTTGTTATA
TCTGTTACCA TCAATCCAGT CATTTATTAT CATATAATAA
```

In the above sequences an ATG start codon follows on at the right-hand or 3'-end.

Just how much of the 5'-non-coding sequence is necessary for efficient promotion is not known precisely. However, experiments can be carried out to answer this question, and In fact some have been performed for VV. These are fully described in the above-mentioned UK Patent Application Publication 2211504A, on pages 12 and 13, the disclosure of which is herein incorporated by reference.

Since some changes In sequence are permissible without loss of the promotional effect, it will be appreciated that it is necessary that the invention should cover sequences which are variant, by substitution as well as by deletion or addition from the non-coding sequences of preferred length up to 160 bp shown above. Incidentally, although the promoter has been referred to herein as an FPV promoter, it will be appreciated that similar 4a genes are virtually certain to be found in other avipoxviruses, such as canarypox or dovepox and to have similar promoters. These are included within the present Invention as being obvious equivalents of FPV.

The recombination vector could contain additional sequence to that herein referred to as promoter DNA. Additional sequence could comprise (a) additional sequence added to the 5'-end of the 60 bp (b) sequence Inserted into the 160 bp without destroying promoter activity or (c) part of the sequence of the FPV gene (inclusive of the ATG initiation codon and onwards), e.g. up to 100 bp thereof.

The above experiments require testing for the efficiency of the promoter. It is not necessary for this purpose to introduce a promoter-gene construct into FPV and monitor expression of the gene product. A shorter method, known as transient assay, is known for use with VV, M. A. Cochran et al., Proc. Natl. Acad. Sci. (USA) 82, 19–23 (1985). In transient assay, the promoter is linked to a gene with an easily assayable product, e.g. the lacZ gene of beta-galactosidase. A plasmid containing this construct is then introduced into a cell which has been infected with the virus. The viral RNA polymerase can transcribe off the promoter, even though the promoter has not been incorporated in the vital genome. Because expression only lasts while both the virus and the plasmid DNA are present in the cell together, this form of expression is known as 'transient'.

In the practice of the invention for poultry, a foreign gene relevant to improving the condition of the poultry would be inserted into the fowlpox virus. Preferably the gene will be one appropriate to an in vivo sub-unit vaccine, for example one or more genes selected from Infectious Bronchitis Virus (IBV), Infectious Bursal Disease Virus, Newcastle Disease Virus (NDV), Marek's Disease Virus, Infectious Laryngotracheitis Virus and genes encoding antigenic proteins of *Eimeria* species. Particular genes of interest are the spike genes of IBV and the HN and F genes of NDV as described in PCT Patent Application Publication No. WO 86/05806 and European Patent Application Publication No. 227414A (both National Research Development Corporation). In order for the foreign gene to be correctly translated in vivo it is necessary for the foreign gene to have its own ATG start codon inserted In the region just following the promoter.

It is necessary to locate a non-essential region (NER) of the FPV, in which to insert the promoter of the invention and the desired foreign gene. In principle, they could be inserted anywhere in the FPV genome which would not harm the basic functions of the virus, or interfere with the action of the FPV promoter or the foreign gene. Preferably the NER is within the terminal inverted repeat of the FPV genome, as described in UK Patent Application Publication No. 2,220,941 or its PCT equivalent Publication No. WO89/12684 both filed on 22 Jun. 1989, the disclosure of which is herein incorporated by reference. Two copies of the foreign gene would then be expected to become inserted in the FPV genome, one towards each end.

The preparation of recombinant and recombination vectors, inoculation of birds and all other methodologies relevant to the invention are as described in the aforesaid prior UK Patent Applications and all such disclosure is herein incorporated by reference for the purpose of brevity.

While the invention its intended primarily for the treatment of chickens it is potentially of interest in relation to other animals which might safely be infected with FPV. It Is even possible that it might be considered safe to infect humans with FPV after appropriate trials have taken place. In that event, the realistic choice of foreign gene would become very wide.

The following Example illustrates the invention.

EXAMPLE

When a FPV random sequence library was compared with the VV 4a protein sequence a number of matches were observed. A "prime-cut" probe was made from one of these, MFP268, which matched closest to the amino-end of the protein (near to the 5' end of the gene and used to probe a library of cloned EcoRI fragments of FPV. A number of positives were observed which contained inserts of approximately 1.8 kb. One of these clones, pMB442, was further characterised by DNA sequencing of random fragments of pMB442 generated by sonication. The sequence of 1434 bp from one of the EcoRI sites is presented in SEQ ID NO: 3, along with a translation of part of the FPV 4a gene open reading frame (ORF). The portion of the 4a gene ORF sequenced is from nucleotides 466 to 1392. The symbols N represent vector nucleotides.)

Shown below is a comparison of the ends of the promoter sequences of VV (SEQ ID NO: 4) and FPV (SEQ ID NO: 5) in front of the genes. Apart from around the ATG start codon where both show the consensus late promoter sequence TAAATG they are not particularly similar.

```
TCA CTG GTA CGG TCG TCA TTT AAT ACT AAA TAA ATG
 •         •    • •• •    ••  •    •   •• •••
CCA TCA ATC CAG TCA TTT ATT ATC ATA TAA TAA ATG
```

In order to test the strength of the FPV 4a promoter, a fragment was cloned from pMB463 using the enzymes BclI and SsPI (pMB463 is the same plasmid as pMB442 but was grown In *E. coli* WK262, a dam minus strain of *E. coli* which allows the DNA to be cleaved by BclI which is inhibited by dam methylation. The BclI and SspI restriction sites TGATCA and AATATT involved in the cloning correspond to positions 246-251 and 481-486 respectively in SEQ ID NO: 3. The DNA was then end-repaired and cloned into SmaI-cut plasmid pNM480, described by Minton, Gene 31 269-273 (1984). The pNM480 plasmid has an EcoRI site to one side of the SmaI site and a HindIII site to the other. It also contains BamHI, SalI and PstI sites between the SmaI and HindIII. After transformation into *E. coli* TG1, colonies which were blue on Xgal Amp plates were screened by mini-DNA preparations and cleavage with EcoRI and HindIII (expected insert about 240 bp).

Two clones, pMB500, pMB501, which appeared to contain only small inserts, were purified on CsCl gradients and the sequences at the insertion sites checked by direct double stranded sequencing using the M13 "minus 40" universal primer. pMB500 contained the 4a promoter from the BclI site, to a point a bit beyond the expected SspI site, namely as far as nucleotide 543, but still in frame. (Why this happened is unclear).

The promoter was then tested in a transient assay system as described in UKPA Publication No. 2211504A but using plasmid pMB500. For comparison, the 4b promoter in plasmid pNM481 (construct pNM4b 30) was also tested. 0.1, 0.3 and 0.5 µg of the plasmid DNA was added 2 hours post infection by FPV strain HP444 (HP438+6 passages) at 1 pfu per cell. The optical densities at 405 nm (proportional to concentration of beta-galactosidase) were as follows:

| Cell background | | 0.017 | |
|---|---|---|---|
| Cell + virus background | | 0.038 | |
| | | 4a | 4b |
| Cell + virus + 0.1 µg plasmid | | 0.198 | 0.277 |
| 0.3 µg plasmid | | 0.386 | 0.388 |
| 0.5 µg plasmid | | 0.459 | 0.558 |

For these results it will be seen that the 4a promoter is approximately as strong a promoter as the 4b.

The 4a promoter can be used in the same way as the 4b, as described in UKPA Publication No. 2211504A.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 20 amino acid residues
        ( B ) TYPE: amino acid ( i i ) MOLECULE TYPE: peptide ( i i i ) HYPOTHETICAL - yes, predicted from fowlpox virus 4a gene.

( v ) FRAGMENT TYPE: N-terminal fragment ( x i ) SEQUENCE DESCRIPTION: SEQ ID NO: 1

```
Met Met Leu Ile Lys Asn Ile Val Thr Leu Asp Gln Leu Glu Ser Ser
 1           5                   10                  15
Asp Tyr Leu Tyr
            20
```

( 2 ) INFORMATION FOR SEQ ID NO: 2:

( i ) SEQUENCE CHARACTERISTICS:
        ( A ) LENGTH: 160 base pairs
        ( B ) TYPE: Nucleic acid
        ( C ) STRANDEDNESS: Double-stranded
        ( D ) TOPOLOGY: Linear ( i i ) MOLECULE TYPE: Genomic DNA
        ( A ) DESCRIPTION: DNA sequence of 160 base pairs
                to the 5'-end of the fowlpox
                virus 4a gene (immediately preceding
                the start codon)

( v i i ) IMMEDIATE SOURCE: Fowlpox Virus 4a gene from Beaudette
                C strain.
        ( A ) LIBRARY: Random sequence library of fowlpox virus
                EcoRI fragments
        ( B ) CLONE: pMB442

( x i ) SEQUENCE DESCRIPTION: SEQ ID NO: 2

```
ACAACATTTA TAGTCTTGAG TGCTGATAAC TGTCCGTTAG TAAGTTCATA GTTTTTATTA   60
CACGGATATA CGTCTTCTGA AAAGGCTGTT AAGTTATATT CTTTGGCTAT ATTTGTTATA  120
TCTGTTACCA TCAATCCAGT CATTTATTAT CATATAATAA                        160
```

( 2 ) INFORMATION FOR SEQ ID NO: 3:

( i ) SEQUENCE CHARACTERISTICS:
        ( A ) LENGTH: 1434 base pairs
        ( B ) TYPE: Nucleic acid
        ( C ) STRANDEDNESS: Double-stranded
        ( D ) TOPOLOGY: Linear ( i i ) MOLECULE TYPE: Genomic DNA
        ( A ) DESCRIPTION: An EcoRI fragment of fowlpox virus
                encoding the region of the 4a gene and
                its promoter ( v i i ) IMMEDIATE SOURCE: Fowlpox virus Beaudette C strain
        ( A ) LIBRARY: Random sequence library of EcoRI fragments
        ( B ) CLONE: pMB442

( x i ) SEQUENCE DESCRIPTION: SEQ ID NO: 3:

```
NNNGAATTCC GATTCTAAGA GGGTTCTTAT TAAAAGGGT GTTTGTAAAA TCTAACAAGT   60
TTTTGCTTTT AGTTTCTTT TTACGAAGTT CGGCAATTTC TTGTTCGAGT AAATGAACCC  120
GTTTATTATC ATCAAATACA GCTGATAAAG AAGGAGTCTG TTGTATATTG TTACTTTGAA  180
TATAATTATC TTTTTCATCG TTGAATGAAT GATGGCTACC TATTTCAGAT ACTATGCAAC  240
GATCATGATC ATCGTCGTCA TTATAAGTTA CATCCTTCTC ATAATTATCT GACCTGGTTG  300
```

-continued

```
TTAATACAAC ATTTATAGTC TTGAGTGCTG ATAACTGTCC GTTAGTAAGT TCATAGTTTT    360

TATTACACGG ATATACGTCT TCTGAAAAGG CTGTTAAGTT ATATTCTTTG GCTATATTTG    420

TTATATCTGT TACCATCAAT CCAGTCATTT ATTATCATAT AATAA ATG ATG TTA        472
                                                  Met Met Leu

ATA AAG AAT ATT GTA ACT CTA GAT CAG TTA GAA TCT TCA GAT TAT CTC      522
Ile Lys Asn Ile Val Thr Leu Asp Gln Leu Glu Ser Ser Asp Tyr Leu
     5              10              15

TAT AAA TTG ATT TCT AGT GTT TTA CCT TCG TTA TGT CTA GAT TAC AAA      570
Tyr Lys Leu Ile Ser Ser Val Leu Pro Ser Leu Cys Leu Asp Tyr Lys
 20              25              30              35

ATA GAT CCA AAA CTA GCG AAT GGA TAC GTA CAT GCG TTA GAT ACT ATA      618
Ile Asp Pro Lys Leu Ala Asn Gly Tyr Val His Ala Leu Asp Thr Ile
             40              45              50

TAC AGT CCA GAA TTA ATT AGT ATA CTT ACA GAC GGT GAA AGA TCA CAA      666
Tyr Ser Pro Glu Leu Ile Ser Ile Leu Thr Asp Gly Glu Arg Ser Gln
         55              60              65

CAG TTA GAT ACA CTG GGT ATT AAT TAC ATT CTT TCC AGA AAA AAT GAT      714
Gln Leu Asp Thr Leu Gly Ile Asn Tyr Ile Leu Ser Arg Lys Asn Asp
     70              75              80

TTA GGT ATT TAT TTT CCT ATA AAT ATC AGA GAA AAC GGA GAA ATA GTA      762
Leu Gly Ile Tyr Phe Pro Ile Asn Ile Arg Glu Asn Gly Glu Ile Val
 85              90              95

TCT ACG TGG AAT AAA AAT ACC GGT GGG TAT ACG AAT CCT ATA CCA TGT      810
Ser Thr Trp Asn Lys Asn Thr Gly Gly Tyr Thr Asn Pro Ile Pro Cys
100             105             110

ACT ATA TCT TTC AAC GAT CTT CCT CCA TTT ACA AAA ATA TTG ATA CAG      858
Thr Ile Ser Phe Asn Asp Leu Pro Pro Phe Thr Lys Ile Leu Ile Gln
             120             125             130

ATA AGA ACC ATG GGT TGT GAG GCT CAC GCT AGA TAC TTC GGT GGA TAC      906
Ile Arg Thr Met Gly Cys Glu Ala His Ala Arg Tyr Phe Gly Gly Tyr
         135             140             145

GTA GAA CAT CCT TCG TCG CCT AAT ATT CTA TCC CCA AAA ATA AAT CCT      954
Val Glu His Pro Ser Ser Pro Asn Ile Leu Ser Pro Lys Ile Asn Pro
     150             155             160

AAT ATC AGT TTT GCA AAT TCT TAC ATA CAT AGT CTT ACT TAT CCA TAT      1002
Asn Ile Ser Phe Ala Asn Ser Tyr Ile His Ser Leu Thr Tyr Pro Tyr
165             170             175

ATA GAG GGA AGA GCT GAT TAT TCT ACT TAC AGA CCA TTG TTG ATT AAT      1050
Ile Glu Gly Arg Ala Asp Tyr Ser Thr Tyr Arg Pro Leu Leu Ile Asn
180             185             190             195

GGT ATT ATG GAA AAG AAG GAT TTA GCT AAT CTG TTG AAT GTA AGA GCG      1098
Gly Ile Met Glu Lys Lys Asp Leu Ala Asn Leu Leu Asn Val Arg Ala
             200             205             210

CTA TTA GAA CCT ATG TCT AGA GCT ATA TTC GAC GCT ATA TTT AAA ATA      1146
Leu Leu Glu Pro Met Ser Arg Ala Ile Phe Asp Ala Ile Phe Lys Ile
         215             220             225

CAA TTT CAT TGT AAC GCT AAT AAC ATT GTA CTT GTA CAA AAT CCT AAT      1194
Gln Phe His Cys Asn Ala Asn Asn Ile Val Leu Val Gln Asn Pro Asn
     230             235             240

ATA GAC ACG GAT CTT ATA ACG ATG CAG ACA CTA AAG TAT CTA GTT ATG      1242
Ile Asp Thr Asp Leu Ile Thr Met Gln Thr Leu Lys Tyr Leu Val Met
245             250             255

TAT TTC CAG CAT TTT TCT GGT TTT ACG TTA AGG GAT ATA TAT TTG GGA      1290
Tyr Phe Gln His Phe Ser Gly Phe Thr Leu Arg Asp Ile Tyr Leu Gly
260             265             270             275

GGA GTA CGA ATA CGT GTT GAT AAT TCT ATG TTA GCG TCT TAT GTT GTA      1338
Gly Val Arg Ile Arg Val Asp Asn Ser Met Leu Ala Ser Tyr Val Val
             280             285             290

TCA ATT TAT TTT AGT AAA GAG ATA AAG TAT ATA GAA GAT AAC AAG TAT      1386
Ser Ile Tyr Phe Ser Lys Glu Ile Lys Tyr Ile Glu Asp Asn Lys Tyr
```

|  | 295 | 300 | 305 |  |
|---|---|---|---|---|
| TTT CGT TAG | ACTATATTGA | TCAGTTTGTA | TTTAGGCCAG ATAATAGCA | 1434 |
| Phe Arg |  |  |  |  |
| 309 |  |  |  |  |

( 2 ) INFORMATION FOR SEQ ID NO: 4:

( i ) SEQUENCE CHARACTERISTICS:
        ( A ) LENGTH: 36 base pairs
        ( B ) TYPE: Nucleic acid
        ( C ) STRANDEDNESS: Double-stranded
        ( D ) TOPOLOGY: Linear ( i i ) MOLECULE TYPE: Genomic DNA
        ( A ) Description: End sequence of the Vaccinia Virus 4a
            gene promoter, up to and including
            start codon.

( x i ) SEQUENCE DESCRIPTION: SEQ ID NO: 4:

TCA CTG GTA CGG TCG TCA TTT AAT ACT AAA TAA ATG ( 2 ) INFORMATION FOR SEQ ID NO: 5:

( i ) SEQUENCE CHARACTERISTICS:
        ( A ) LENGTH: 36 base pairs
        ( B ) TYPE: Nucleic acids
        ( C ) STRANDEDNESS: Double-stranded
        ( D ) TOPOLOGY: Linear ( i i ) MOLECULE TYPE: Genomic DNA
        ( A ) DESCRIPTION: End sequence of the fowlpox virus 4a
            gene promoter, up to and including
            start codon.

( x i ) SEQUENCE DESCRIPTION: SEQ ID NO: 5:

CCA TCA ATC CAG TCA TTT ATT ATC ATA TAA TAA ATG

We claim:

1. An isolated DNA consisting essentially of the promoter sequence which is located immediately to the 5'-end of a gene in the fowlpox virus genome, said gene being designated the FP4a gene and identified as that which encodes a protein of 800–1000 amino acids in a sequence beginning with the sequence Met Met Leu Ile Lys Asn Ile Val Thr Leu Asp Gln Leu Glu Ser
1        5              10              15
                            Ser Asp Tyr Leu Tyr.
                            20

2. DNA according to claim 1 wherein the promoter sequence is of length up to 160 nucleotides.

3. DNA according to claim 2 wherein the promoter sequence is of length up to 100 nucleotides.

4. DNA according to claim 2, wherein said 160 nucleotides are

```
ACAACATTTA TAGTCTTGAG TGCTGATAAC TGTCCGTTAG TAAGTTCATA GTTTTTATTA   60
CACGGATATA CGTCTTCTGA AAAGGCTGTT AAGTTATATT CTTTGGCTAT ATTTGTTATA  120
TCTGTTACCA TCAATCCAGT CATTTATTAT CATATAATAA.                       160
```

5. Recombinant DNA comprising the promoter sequence which is located immediately to the 5'-end of a gene in the fowlpox virus genome, said gene being designated the FP4a gene and identified as that which encodes a protein of 800–1000 amino acids in a sequence beginning with the sequence Met Met Leu Ile Lys Asn Ile Val Thr Leu Asp Gln Leu Glu Ser Ser
1           5                   15                  15

Asp Tyr Leu Tyr,
              20 transcribably linked to a foreign gene.

6. Recombinant DNA according to claim 5 wherein the promoter sequence is of length up to 160 nucleotides.

7. Recombinant DNA comprising a non-essential region (NER) sequence of fowlpox virus interrupted by DNA according to claim 5.

8. A recombinant cloning vector comprising DNA according to claim 7 and vector sequence.

* * * * *